US006231536B1

(12) United States Patent
Lentz

(10) Patent No.: US 6,231,536 B1
(45) Date of Patent: May 15, 2001

(54) METHOD AND COMPOSITIONS FOR TREATMENTS OF CANCERS

(76) Inventor: M. Rigdon Lentz, 6347 Shadow Ridge Ct., Brentwood, TN (US) 37027

(*) Notice: Subject to any disclaimer, the term of this patent is extended or adjusted under 35 U.S.C. 154(b) by 0 days.

(21) Appl. No.: 09/316,226

(22) Filed: May 21, 1999

Related U.S. Application Data

(63) Continuation-in-part of application No. 09/083,307, filed on May 22, 1998.

(51) Int. Cl.[7] .......................... A61M 37/00; A61B 19/00; B01D 11/00; A61K 39/00
(52) U.S. Cl. ...................... 604/5.04; 604/4.01; 604/5.01; 604/5.02; 128/898; 210/650; 424/140.1; 424/145.1; 424/529
(58) Field of Search .................................. 604/4–6, 4.01, 604/5.01, 5.02, 5.04, 6.04; 128/898; 210/638, 645–646, 650–651, 767, 252; 424/9.1, 484, 486, 489–491, 78.08, 78.1, 85.1, 85.2, 85.4, 85.7, 85.5, 130.1, 133.1, 134.1, 140.1, 141.1, 148.1, 145.1, 177.1, 529

(56) References Cited

U.S. PATENT DOCUMENTS

| 4,486,282 | 12/1984 | Bier . | |
| 4,708,713 | * 11/1987 | Lentz | ................................... 604/5.01 |
| 5,135,919 | 8/1992 | Folkman et al. . | |

(List continued on next page.)

OTHER PUBLICATIONS

Chen et al., Journal of Neuropathology and Experimental Neurology, 1997.*
Chen, et al., "Soluble TNF—Receptors constitutively shed and downregulate adhesion molecule expression in malignant gliomas," *J. Neuropathol. Exp. Neurol.* 56(5):541–550 (1997).
Colman, et al., *Hemostasis and Thrombosis: Basic Principles and Clinical Practice* (2nd Ed.), p. 263, J.B.Lippincott;Philadelphia, PA, 1987.
Jablonska & Peitruska, "Release of soluble tumor necrosis factor receptors from polymorphonuclear cells of breast cancer patients," *Arch. Immunol Ther Exp* (Warsz). 45(5–6):449–53 (1997).
Matschiner, et al., *Current Advances in Vitamin K Research*, pp. 135–140, (John W. Suttie, ed.) Elsevier Science Publishing Co., Inc., 1988.

*Primary Examiner*—Angela D. Sykes
*Assistant Examiner*—Patricia Blanco
(74) *Attorney, Agent, or Firm*—Arnall Golden & Gregory, LLP

(57) ABSTRACT

A method to treat cancer uses ultrapheresis, refined to remove compounds of less than 120,000 daltons molecular weight, followed by administration of replacement fluid, to stimulate the patient's immune system to attack solid tumors. In the preferred embodiment, the patient is ultrapheresed using a capillary tube ultrafilter having a pore size of 0.02 to 0.05 microns, with a molecular weight cutoff of 120,000 daltons, sufficient to filter one blood volume. The preferred replacement fluid is ultrapheresed normal plasma. The patient is preferably treated daily for three weeks, diagnostic tests conducted to verify that there has been shrinkage of the tumors, then the treatment regime is repeated. The treatment is preferably combined with an alternative therapy, for example, treatment with an anti-angiogenic compound, one or more cytokines such as TNF, gamma interferon, or IL-2, or a procoagulant compound. The treatment increases endogenous, local levels of cytokines, such as TNF. This provides a basis for an improved effect when combined with any treatment that enhances cytokine activity against the tumors, for example, treatments using alkylating agents, doxyrubicin, carboplatinum, cisplatinum, and taxol. Alternatively, the ultrapheresis treatment can be combined with local chemotherapy, systemic chemotherapy, and/or radiation.

19 Claims, 2 Drawing Sheets

U.S. PATENT DOCUMENTS

| | | |
|---|---|---|
| 5,147,638 | 9/1992 | Esmon et al. . |
| 5,290,807 | 3/1994 | Folkman et al. . |
| 5,523,096 * | 6/1996 | Okarma et al. .................. 424/489 |
| 5,629,327 | 5/1997 | D'Amato . |
| 5,639,725 | 6/1997 | O'Reilly et al. . |
| 5,679,260 | 10/1997 | Boos et al. . |
| 5,698,586 | 12/1997 | Kishimoto et al. . |
| 5,712,291 * | 1/1998 | D'Amato .......................... 514/323 |
| 5,713,491 | 2/1998 | Hughes et al. . |
| 5,716,981 | 2/1998 | Hunter et al. . |
| 5,733,876 | 3/1998 | O'Reilly et al. . |
| 5,861,483 * | 1/1999 | Wolpe .............................. 530/385 |
| 5,919,898 * | 7/1999 | Nakatani et al. ................. 530/345 |
| 5,980,887 * | 11/1999 | Isner et al. ....................... 424/93.7 |

* cited by examiner

METHOD AND COMPOSITIONS FOR TREATMENTS OF CANCERS

This application is a CIP of U.S. Ser. No. 09/083,307 filed May 22, 1998.

BACKGROUND OF THE INVENTION

The present invention is generally in the field of enhancing an immune response, and particularly relates to the removal of inhibitors of immune mediators, in combination with anti-angiogenic compounds, cytokines, compounds inducing a procoagulant state, chemotherapeutics and/or radiation.

Conventional cancer therapy is based on the use of drugs and/or radiation which kills replicating cells, hopefully faster than the agents kill the patient's normal cells. Surgery is used to reduce tumor bulk, but has little impact once the cancer has metastasized. Radiation is effective only in a localized area.

The treatments can in themselves kill the patient, in the absence of maintenance therapy. For example, for some types of cancer, bone marrow transplants have been used to maintain the patient following treatment with otherwise fatal amounts of chemotherapy. Efficacy has not been proven for treatment of solid tumors, however. "Cocktails" of different chemotherapeutic agents and combinations of very high doses of chemotherapy with restorative agents, for example, granulocyte macrophage colony stimulating factor ("GM-CSF"), erythropoietin, thrombopoetin granulocyte stimulating factor, ("G-CSF"), macrophage colony stimulating factor ("M-CSF") and stem cell factor ("SCF") to restore platelet and white cell levels, have been used to treat aggressive cancers. Even with the supportive or restrictive therapy, side effects are severe.

Other treatments have been tried in an attempt to improve mortality and morbidity. Vaccines to stimulate the patient's immune system have been attempted, but not with great success. Various cytokines, alone or in combination, such as tumor necrosis factor, interferon gamma, and interleukin-2 ("IL-2") have been used to kill cancers, but have not produced cures. More recently, anti-angiogenic compounds such as thalidomide have been tried in compassionate use cases and shown to cause tumor remission. In animal studies, compounds inducing a procoagulant state, such as an inhibitor of protein C, have been used to cause tumor remission. New studies have shown that inhibitors of cytokine receptors, such as tumor necrosis factor receptors ("TNFRs") which are released in a soluble form from tumor cells, in high concentrations relative to normal cells, may restore the immune system's attack on the tumor cells (Jablonska and Peitruska, Arch. Immunol. Ther. Exp. (Warsz) 1997, 45(5–6), 449–453; Chen, et al., J. Neuropathol. Exp. Neurol. 1997, 56(5), 541–550).

U.S. Pat. No. 4,708,713 to Lentz describes an alternative method for treating cancer, involving ultrapheresis to remove compounds based on molecular weight, which promotes an immune attack on the tumors by the patient's own white cells.

Despite all of these efforts, many patients die from cancer; others are terribly mutilated. It is unlikely that any one therapy will be effective to cure all types of cancer.

It is therefore an object of the present invention to provide a method and compositions for treatment of solid tumors.

It is a further object of the present invention to provide a method and compositions that does not involve non-selective, extremely toxic, systemic chemotherapy.

SUMMARY OF THE INVENTION

A method to treat cancer uses ultrapheresis, refined to remove compounds of less than 120,000 daltons molecular weight, followed by administration of replacement fluid, to stimulate the patient's immune system to attack solid tumors. In the preferred embodiment, the patient is ultrapheresed using a capillary tube ultrafilter or parallel plate filter having a molecular weight cutoff of 120,000 daltons, sufficient to filter at least one blood volume. The preferred replacement fluid is ultrapheresed normal plasma. Alternatively, the patient is pheresed to selectively remove soluble receptor/inhibitors to soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), or soluble interferon-gamma receptor ("sIFN-gammaR"). These can be removed by binding to the cytokine, an epitope thereof, or an antibody to the receptor. These can be immobilized in the filter, in a column, or using other standard techniques for binding reactions to remove proteins from the blood or plasma of a patient. The patient is preferably treated daily for three weeks, diagnostic tests conducted to verify that there has been shrinkage of the tumors, then the treatment regime is repeated.

The treatment is preferably combined with an alternative therapy, for example, treatment with an anti-angiogenic compound, one or more cytokines such as TNF, gamma interferon, other interferons, or IL-2, or a procoagulant compound. The treatment increases the inflammation against tumors by allowing cytokines, such as TNF, to work effectively. This provides a basis for an improved effect when combined with any treatment that enhances cytokine activity against the tumors, for example, treatments using alkylating agents, doxyrubicin, carboplatinum, cisplatinum, and taxol, and other drugs which may be synergistic in effect with "unblocked" cytokines. Alternatively, the ultrapheresis treatment can be combined with local chemotherapy, systemic chemotherapy, and/or radiation.

DETAILED DESCRIPTION OF THE INVENTION

Figure 1:
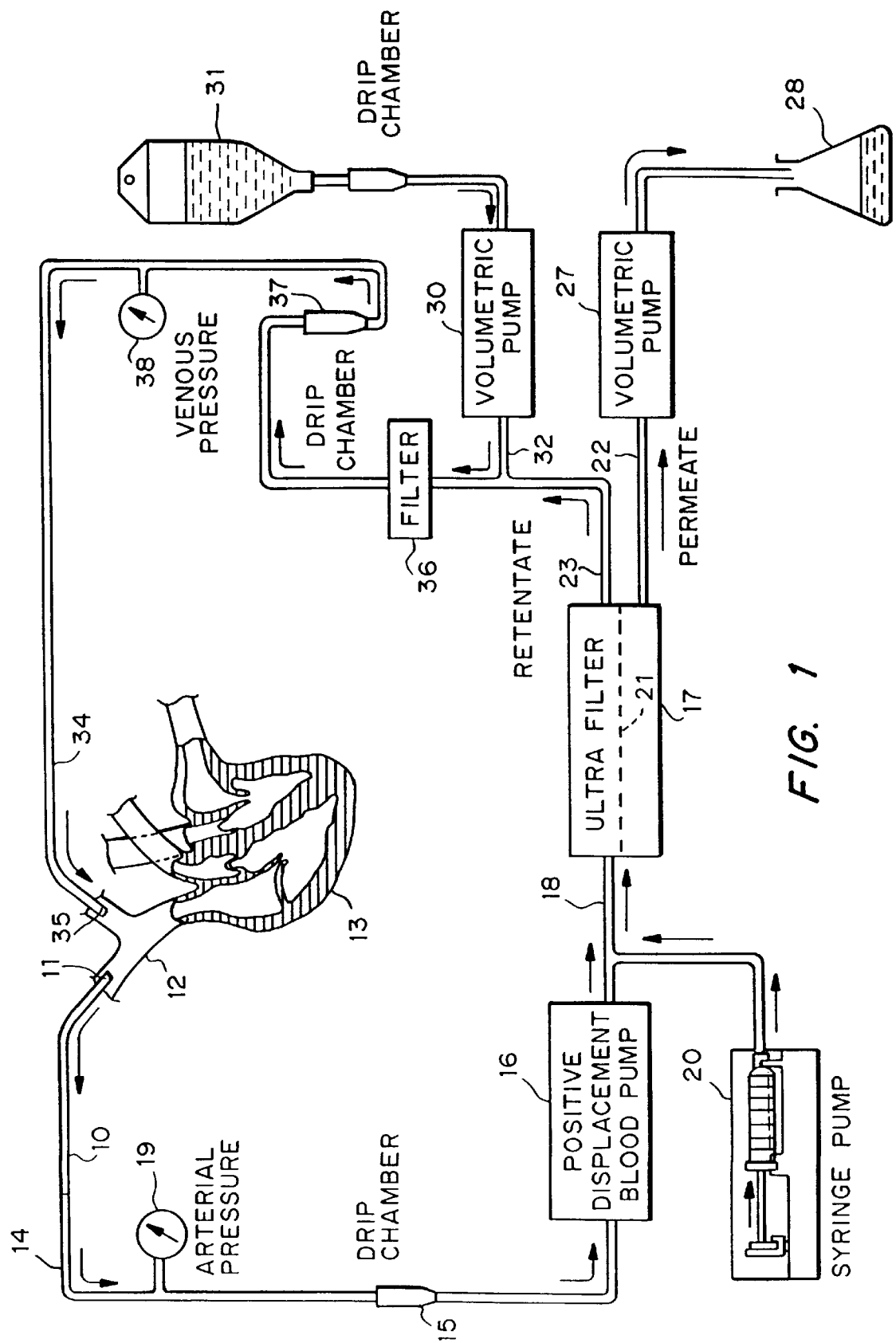
FIGS. 1 and 2 are schematics of the system for ultrapheresis.

The methods and devices disclosed herein are useful for treatment of patients with cancer, immune-mediated disorders, chronic parasitism, some viral diseases, and other disorders characterized by elevated levels of TNF receptors or inhibitors to IL-2, IL-6, gamma interferon, or other pro-inflammatory signals as well as white cell activation. Examples demonstrate efficacy in treating cancer patients.

I. Ultrapheresis

A. Ultrapheresis System

1. Filters

The filter must be biocompatible, and suitable for contact with blood, without causing excessive activation of platelets or clotting. Devices will typically be either parallel plate filters or capillary membrane filters. These can be adapted from devices currently in use for kidney dialysis. The capillary membrane filters will typically have a surface area of between about 0.25 and 1 $m^2$ for use with children and between about 1 and 3 $m^2$ for use with adults. The parallel plate filters will typically have a surface area in the range from 0.1 and 2 $cm^2$/ml of blood to be filtered.

The filter membranes will typically be a biocompatible or inert thermoplastic such as polycarbonate, polytetrafluoroethylene (Teflon®), polypropylene, ethylene polyvinyl alcohol or polysulfone, having a pore size typically of between 0.02 and 0.05 microns in a capillary membrane filter and of between 0.04 and 0.08 microns in a parallel plate filter. The actual pore size that yields the desired cutoff of approximately 120,000 daltons is determined based on the fluid flow geometry, shear forces, flow rates, and surface area. The effective cutoff for a capillary membrane filter with a pore size of 0.03 microns is 120,000 daltons, with a sieving coefficient of between 10 and 30%. This results in only a trivial amount of IgG being removed from the patient's blood. The filter membrane should be less than about 25 microns, preferably less than about 10 microns, thick. The permeable membrane should not cause blood clotting or otherwise react with the blood.

A preferred membrane is one in which the pores are made by electron beams directed perpendicularly to the surface because the size and density of the pores can be accurately controlled in this manner. The pores are essentially circular in cross section so the effective pore size is the actual pore size. The effective pore size of ultrafiltered media having pores with non-circular cross sections shall be the diameter of a circular pore which will pass molecules or other components of an equivalent size to the molecules or other components which pass through the filter medium in question.

Suitable devices can be obtained from Asahi Chemical Company, Japan, and Kuraray Co., Ltd, 1-12-39, Umeda, ite-ku, Osaka 530, Japan.

Staged filters can also be used, which have different pore sizes and/or geometries or surfaces areas, to provide for a "staggered" removal of materials from the blood. Alternatively, although not at this time preferred, one can use differential centrifugation, to provide for an appropriate separation of blood components. Specific absorbing columns can also be employed to selectively remove specific cytokine and cellular inhibitors from the filtered plasma so that the ultrafiltrate (treated plasma) can be returned to the patient.

2. Process Controls and Fluid Handling

The patient will typically be connected to the blood processing device using standard intravenous tubing, with connections similar to those used for plateletpheresis, so that blood can be removed from the patient at one site and returned at another. The tubing is connected to a pump that controls the flow rate so that in the preferred embodiment one blood volume (based on approximately 7% of the total body weight) is processed over a period of approximately 2½ hours. The filtrate is then returned from the filtration device to the patient at the second site. Standard microprocessor controls can be used to regulate the blood flow, for example, by monitoring the volume of the blood products being removed, in combination with flow rate monitors and pump speed.

The entire system should first be flushed with saline and then treated with an anticoagulant or anticlotting agent, such as sodium heparin, to be sure that there are no locations within the system where blood clotting can occur. Moreover, small amounts of anticoagulants should be continually introduced into the blood stream directed to the ultrafilter to ensure than no clotting occurs during the filtration process. All of the surfaces of the system which come in contact with the blood and fluids which are infused into the patient must be sterilized prior to commencing treatment.

FIG. 1 illustrates a system for ultrapheresis. Blood is removed from a patient by means of a venous catheter 10 with the distal lead 11 thereof disposed in the superior vena cava 12 leading to the patient's heart 13. The blood passes through conduit 14 to a drip chamber 15 and then into pump 16 which controls the pressure of the blood to the separation unit 17, preferably an ultrafilter as shown, through conduit 18. A pressure gauge 19 is provided on conduit 14 to continually monitor arterial pressure. A syringe pump 20 feeds an anti-clotting drug such as sodium heparin to conduit 18 to prevent the clotting of blood in the ultrafilter 17. In the ultrafilter 17 the blood stream passes over the ultrafilter medium or membrane 21 under pressure. The blood fraction including the low molecular weight components passes through the membrane 21 and is discharged as permeate through conduit 22. The retentate or treated blood containing the high molecular weight components, which include whole blood cells and platelets, is discharged into conduit 23 which ultimately leads back to the patient. Volumetric pump 27 passes a controlled amount of permeate to a container 28 for containment and for measuring. Volumetric pump 30, which is preferably the same type and capacity as pump 27, pumps replacement fluid from a container 31 to conduit 32, which directs the fluid to conduit 23 where it mixes with the retentate or treated blood. The treated blood and other components are returned to the patient through venous catheter 34, the distal or discharge end of which is disposed in the brachiocephalic vein. The volumetric pumps 27 and 30 are preferably set either to pump the same total amount of fluid or to pump at the same rate, so that the same volume of fluid which is removed from the patient's blood stream as permeate is returned as replacement fluid. The blood stream in conduit 23 is passed through filter 36 to remove clots or other debris from the blood stream. A drip chamber 37 ensures that no significant quantities of air enter the patient's blood stream. A pressure gauge 38 is provided to continually monitor venous blood pressure.

Figure 2:
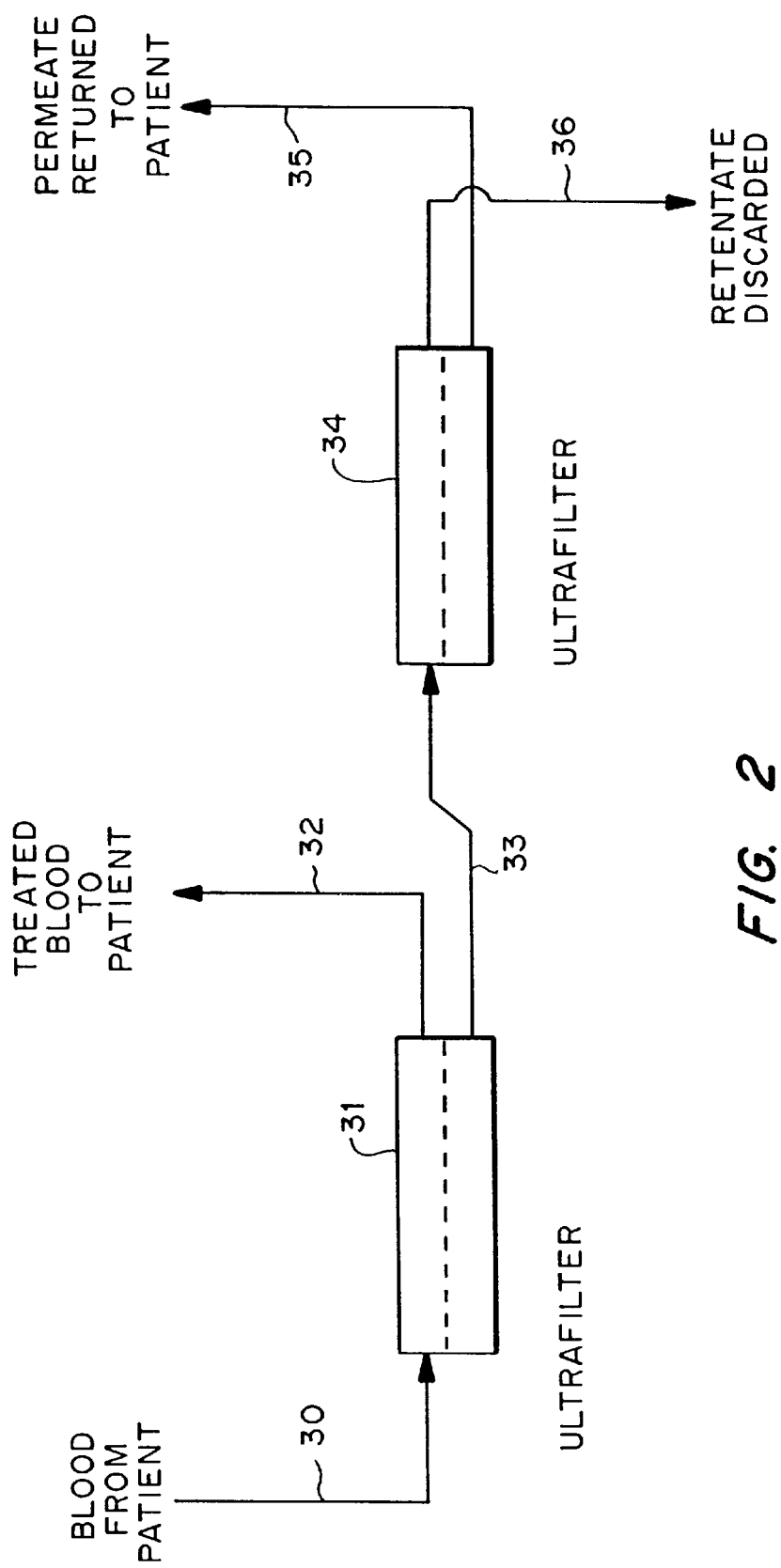

FIG. 2 illustrates another embodiment wherein blood removed from a patient is first passed through conduit 30 to a first ultrafilter 31 to selectively separate a blood fraction with components having molecular weights less than about 1,000,000 Daltons. The retentate from this ultrafiltration which contains the high molecular weight components is returned through conduit 32 to the patient. The permeate from the first ultrafilter 31 is passed through conduit 33 to a second ultrafilter 34 where a blood fraction having a molecular weight below 30,000 is removed from the permeate stream from the first ultrafilter 31. The permeate from the second ultrafilter 34, which contains the very low molecular weight components such as salts and nutrients may be returned to the patient through conduit 35. The retentate from the second ultrafilter which contains blocking factors, IgG immunoglobulins and other components is discharged through conduit 36.

Blood should be pumped through the ultrafilter unit at sufficient pressure to cause the blood components having the immunosuppressive effects to pass through the filter but at a velocity which will not excessively shear or otherwise damage the blood cells passing over the membrane. Generally it has been found that the ratio of the area of the membrane to the amount of blood treated per hour should be within about 0.1 to 2 cm/mL. Differential pressure across the membrane should range from about 2 to 20 mM Hg.

3. Replacement Fluids

The patient must receive replacement fluids following filtration. The preferred replacement fluid is ultrapheresis normal plasma, for example, expired plasma obtained from the Red Cross, which has been filtered using the same filter as used to treat the patient. Alternatively, the patient can be administered normal albumin, or fresh frozen plasma diluted with saline.

II. Treatment with Adjuvant Therapies

Standard ultrapheresis is conducted over a period of time until a positive indication is observed. This is typically based on diagnostic tests which show that there has been some reduction in tumor size or which suggests tumor inflammation. The patient is preferably treated daily for three weeks, diagnostic tests conducted to verify that there has been shrinkage of the tumors and/or inflammation, then the treatment regime is repeated.

Surgical (or vacuum) removal of necrotic material may be required prior to or during treatment to avoid toxicity associated with high tumor burden.

This procedure has been demonstrated to cause a significant response (greater than 50% reduction in size of tumors) in a variety of solid tumors in approximately 50% of patients who have failed all other treatment modalities. A tumor specific inflammatory response provoked by ultrapheresis has been documented in approximately 75% of patients in metastatic melanoma clinical trials. This inflammation is characterized by redness, swelling, warmth, and tenderness and is confined to tumors only. There has been no associated injury to non-cancerous tissue. This tumor specific inflammatory response has led to a 50% or greater reduction in the size of tumors in 50% of patients studied so far. Clinical trials have also demonstrated a 44% major reduction of tumor metastases in human breast cancer and prostate cancer.

Tumor specific inflammation has been observed in patients with metastatic colon cancer, ovarian cancer, lung cancer, head and neck cancer, cervical and endometrial cancers. In some cases, this inflammation has been followed by significant tumor regressions in each tumor type. The significance of response in such diverse tumor types strongly suggests that ultrapheresis modifies the patient's response to the tumor in favor of successful immunologic control of the tumor. Types of tumors that are particularly sensitive to the ultrapheresis include epithelial tumors, sarcomas, melanomas and glioblastomas.

It would clearly be advantageous to cause complete remissions. Based on the presumed mechanism that the process is removing immune inhibitors produced by the tumors, especially inhibitors of cytokines and other immune mediators, it is possible to treat the patients with adjuvant or combination therapies, that enhance the results achieved with the ultrapheresis. TNF-alpha and beta receptors are thought to be particularly important immune inhibitors. Therefore, compounds which enhance TNF activity are particularly preferred. These include anti-angiogenic compounds, such as thalidomide, procoagulant compounds, cytokines and other immunostimulants. Standard chemotherapeutic agents and/or radiation can also be used with the ultrapheresis.

A. Anti-Angiogenic Compounds

Any anti-angiogenic compound can be used. Exemplary anti-angiogenic compounds include O-substituted fumagillol and derivatives thereof, such as TNP-470, described in U.S. Pat. Nos. 5,135,919, 5,698,586, and 5,290,807 to Kishimoto, et al.; angiostatin and endostatin, described in U.S. Pat. Nos. 5,290,807, 5,639,725 and 5,733,876 to O'Reilly; thalidomide, as described in U.S. Pat. Nos. 5,629,327 and 5,712,291 to D'Amato; and other compounds, such as the anti-invasive factor, retinoic acid, and paclitaxel, described in U.S. Pat. No. 5,716,981 to Hunter, et al., and the metalloproteinase inhibitors described in U.S. Pat. No. 5,713,491 to Murphy, et al. Thalidomide is administered once daily, 200 mg orally.

B. Procoagulant Compounds

Protein C is a vitamin K-dependent plasma protein zymogen to a serine protease. Upon activation it becomes a potent anticoagulant. Activated protein C acts through the specific proteolysis of the procoagulant cofactors, factor VIIIa and factor Va. This activity requires the presence of another vitamin K-dependent protein, protein S, calcium and a phospholipid (presumably cellular) surface. As described in *Hemostasis and Thrombosis: Basic Principles and Clinical Practice* 2nd Ed., Colman, R. W., et al.,p. 263 (J. B. Lippincott, Philadelphia, Pa. 1987), protein C circulates in a two-chain form, with the larger, heavy chain bound to the smaller light chain through a single disulfide link. Protein C is activated to activated protein C (APC). Thrombin is capable of activating protein C by the specific cleavage of the $Arg^{12}$-$Leu^{13}$ bond in the heavy chain. In vivo, in the presence of physiological concentrations of calcium, the rate of this activation is enhanced dramatically when thrombin is bound to the endothelial cell cofactor, thrombomodulin. Matschiner, et al., *Current Advances in Vitamin K Research*, pp. 135–140, John W. Suttie, ed. (Elsevier Science Publishing Co., Inc. 1988) have further reviewed the role of the Vitamin K dependent proteins in coagulation.

Blockage of the natural anticoagulant pathways, in particular the protein C pathway, uses the natural procoagulant properties of the tumor to target the tumor capillaries for microvascular thrombosis, leading to hemorrhagic necrosis of the tumor, as described in U.S. Pat. No. 5,147,638 to Esmon, et al.

Examples of such compounds include anti-protein C and anti-protein S.

C. Cytokines

The biologic activity and clinical effectiveness of pro-inflammatory cytokines is augmented by ultrapheresis in the patient with cancer and other states of acquired immune tolerance Specifically, both TNF alpha and TNF beta, in doses of between approximately 100 to 500 micrograms per meter squared body surface area (M2BSA), can enhance the immune reaction in aggressive tumors. Monocyte and lymphocyte activation is augmented by INF-alpha, INF-beta and gamma. The IL-1 and IL-2 receptor antagonists are removed by ultrapheresis and thereby upregulate the in vivo activity of these cytokines. An 80 kD glycoprotein, which is responsible for inhibiting blastoid transformation in advanced malignancy, chronic infectious disease and pregnancy, has recently been found, and appears to be responsible for the loss of delayed hypersensitivity reactions in these diseases, which is removed by this process. This is significant because in removing this type of suppression, vaccines of all types will work better. Dosage regimes for IFN-alpha and beta are 3 M units subcutaneous three times a week up to 20 M units/M2 BSA daily. Interferon-gamma is administered in a dosage of between 100 to 1000 micgms per day.

D. Anti-cytokine receptor molecules.

It is well established that TNF receptor 1 and TNF receptor 2 molecules are shed by tumor cells, and that these molecules appear to inhibit immune mediated attack by the host on the tumor cells. The ultrapheresis is believed to remove the majority of these soluble receptors. Additional, and/or selective, removal of these soluble receptor/inhibitors to soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), or soluble interferon-gamma receptor ("sIFN-gammaR") can be used to supplement or instead of the ultrapheresis. The advantage of selective removal is that the same beneficial effect is obtained in treatment of the disorder but the treatment is much less expensive and safer since exogenous plasma or albumin does not have to be administered to the patient when there is selective removal. These can be removed by binding to the cytokine, an epitope thereof, or an antibody to the receptor. These can be immobilized in the filter, in a column, or using other standard techniques for binding reactions to remove proteins from the blood or plasma of a patient. As used herein, antibody refers to antibody, or antibody fragments (single chain, recombinant, or humanized), immunoreactive against the receptor molecules. In the preferred embodiment, these antibodies are immobilized on the ultrapheresis membrane filters, using standard antibody coupling techniques. In the most preferred embodiment, the antibody is reactive with the carboxy-terminus of the shed receptor molecules, thereby avoid concerns with signal transduction by the receptor is still present on the cell surface.

E. Chemotherapeutic Agents

Preferred chemotherapeutic agents are those which are synergistic with TNF, for example, alkylating agents, doxyrubicin, carboplatinum, cisplatinum, and tomoxifen. Tamoxifen plays a role not only in blocking of estrogen receptors but also certain growth factor receptors such as epidermal derived growth factor ("EDGF"), fibroblast derived growth factor ("FDGF"), tumor derived growth factor ("TDGF"), TDGF-$\beta$ and platelet derived growth factor ("PDGF") and therefore may be complementary to inflammation against cancers provoked by ultrapheresis.

F. Radiation

Radiation therapy is destructive of normal tissue, causing tumors to die partially by an inflammatory attack. Ultrapheresis allows the use of lower doses of radiation to kill residual tumor cells and spare normal tissue. In a preferred method, ultrapheresis is used as the initial therapy, followed by radiation at approximately one-half of the normal dosages. It is well established that TNF kills tumor cells by generating free oxygen radicals, hydroxyl radicals and halide ions, and that radiation therapy generates carbonium ions in tissue. Therefore the combination of the two is more effective in killing cancer cells than either alone.

III EXAMPLES

Example 1

Treatment of a Patient with Metastatic Leiomyoscarcoma with Ultrapheresis

Mrs. J. K. is a 43 year old lady with metastatic leiomyoscarcoma with six (6) lung metastases all of which developed within one month of surgery on both lungs to remove tumors. These tumors had also failed methotrexate, adriamycin, ifosphomide, and dactinomycin.

She received 24 ultrapheresis procedures with no side effects. One month later, CAT scan revealed only four (4) tumors and these were reduced in size by 50%.

Example 2

Treatment of Patients with Breast Cancer by Ultrapheresis and Thalidomide

Mrs. J. R. is a 44 year old lady who had metastatic breast cancer that had failed radiation therapy and treatment with chemotherapeutic agents: cytoxan, adriamycin, 5-FU, taxol, cis-platin, navalbine, tamoxofin and arimedex. Tumor at the time of ultrapheresis was documented in lungs, bone and skin of the entire left anterior and lateral chest.

She was treated with 15 ultrapheresis procedures over a three week period. She experienced marked inflammation in the tumors of his skin, increased pain from the tumors in her bones, and swelling of the tumors in her lungs. She then received the drug thalidomide 200 mg at night. The redness and swelling in her skin improved within 2 days and her breathing returned to normal within one week. Two weeks after completing treatment, all tumor in her skin had resolved clinically, her bone pain resolved and the tumors in her lungs resolved on repeat CAT scan. One week later, she returned to work as a school counselor. She tested disease free two months after treatment and was being maintained on thalidomide at the same dose.

Example 3

Treatment of Patient with Metastic Melanoma with Ultrapheresis and Thalidomide

Mr. P. G. is a 54 year old engineer with metastatic melanoma with metastases to lung and to lymph nodes in the mediastinum.

He received 24 ultrapheresis procedures, resulting in a 25% reduction of tumors. He was subsequently treated with an additional 12 procedures, resulting in minor tumor reduction despite evidence of tumor inflammation. The tumors regrew within one month. He was again retreated with ultrapheresis, again resulting in inflammation and some minor regression, but was then treated with thalidomide at the time of tumor inflammation. Two months later, repeat CAT scan showed complete disappearance of tumors in the lung and mediastinum. He is being followed closely and shows no evidence of disease and has no medical complaints six months after completing treatment.

Example 4

Treatment of a Patient with Metastic Adenocarcinoma with Ultrapheresis and Thalidomide Dr. R. S. is a 59 year old gentlemen with metastatic adenocarcinoma of the left upper lung with metastases to liver, brain and bones. His tumors had failed to respond to taxol, cis-platin and etoposide. His brain tumors had responded to radiation therapy.

He received 15 ultrapheresis procedures. Each procedure caused increased pain in tumors of his spine, pelvis, right hip and left shoulder. Follow up scans after ultrapheresis treatment revealed resolution of tumors in pelvis, spine, hip, and ribs. There was a 50% reduction in the primary tumor in the lung and liver. Thalidomide was then started at 200 mg each night. One month later, the scans revealed further reduction in the tumors in lung and liver. The patient's pains have all been resolved and he is asymptomatic at this time.

Modifications and variations of the method and compositions described herein will be obvious to those skilled in the art. Such modifications and variations are intended to come within the scope of the appended claims.

I claim:

1. A method for inducing an immune response against transformed, infected or diseased tissue in a patient comprising removing soluble cytokine receptor molecules selected from the group consisting of soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), and soluble interferon-gamma receptor ("sIFN-gammaR") in the blood of the patient having a molecular weight of 120,000 daltons or less, until the transformed, infected, or diseased tissue is reduced in amount.

2. The method of claim 1 wherein the tissue is a solid tumor.

3. The method of claim 1 wherein the components are removed from one blood volume.

4. The method of claim 1 wherein the components are removed in multiple treatments.

5. The method of claim 1 wherein the soluble cytokine receptor molecules are removed by binding of the molecules to a filter.

6. The method of claim 5 wherein the soluble cytokine receptor molecules are selected from the group consisting of soluble tissue necrosis factor receptor-1 ("sTNFR-1") and soluble tissue necrosis factor receptor-2 ("sTNFR-2").

7. The method of claim 6 wherein the cytokine receptor molecules are removed by binding to the cytokine or to an antibody or antibody fragment immunoreactive with the cytokine receptor molecules.

8. The method of claim 7 wherein the cytokine or antibody or antibody fragments are immobilized in a filter or column through which the patient's blood or plasma is circulated prior to being returned to the patient.

9. The method of claim 1 further comprising vaccinating the patient with a vaccine against the transformed, infected or diseased tissue.

10. A system for inducing an immune response against transformed, infected or diseased tissue comprising a device for removing only components present in the blood having a molecular weight of 120,000 daltons or less, having inlet and outlet means for connection to a pump and tubing to recirculate the blood of a patient through the device, having immobilized therein absorbents selectively removing specific cytokine or cellular inhibitors selected from the group consisting of soluble tissue necrosis factor receptor-1 ("sTNFR-1"), soluble tissue necrosis factor receptor-2 ("sTNFR-2"), soluble interleukin-2 receptor ("sIL-2R"), soluble interleukin-1 receptor ("sIL-1R"), soluble interleukin-6 receptor ("sIL-6R"), and soluble interferon-gamma receptor ("sIFN-gammaR") from the blood.

11. The system of claim 10 wherein the device is a capillary membrane filter with a pore size of between about 0.02 and 0.05 microns.

12. The system of claim 10 wherein the device is a parallel plate filter with a pore size of between about 0.04 and 0.08 microns.

13. The system of claim 10 wherein the device comprises filters with different pore sizes or geometries to provide for staggered removal of materials from the blood.

14. The system of claim 10 wherein the device is an absorbent column selectively removing specific cytokine or cellular inhibitors from the blood.

15. The system of claim 14 wherein the cytokine or cellular inhibitors are selected from the group consisting of soluble tissue necrosis factor receptor-1 ("sTNFR-1") and soluble tissue necrosis factor receptor-2 ("sTNFR-2").

16. The system of claim 15 comprising cytokines or antibody or antibody fragments immunoreactive with the cytokine receptor molecules.

17. The system of claim 16 wherein the cytokine or antibody or antibody fragments are immobilized in a filter or column through which the patient's blood or plasma is circulated prior to being returned to the patient.

18. The system of claim 10 wherein the blood is plasma.

19. The system of claim 10 wherein the system includes means for administering radiation to the tissue.

* * * * *